(12) United States Patent
Le Prado et al.

(10) Patent No.: US 10,126,379 B2
(45) Date of Patent: Nov. 13, 2018

(54) MAGNETOMETER WITHOUT SLAVING AND WITH COMPENSATION FOR FLUCTUATIONS IN THE RESONANCE GRADIENT IN WEAK FIELD, MAGNETOMETERS NETWORK AND MEASUREMENT METHOD

(71) Applicant: Commissariat A L'Energie Atomique et aux Energies Alternatives, Paris (FR)

(72) Inventors: Matthieu Le Prado, Saint Marcellin (FR); Jean-Michel Leger, Villard Bonnot (FR); Sophie Morales, Varces (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 520 days.

(21) Appl. No.: 14/856,950

(22) Filed: Sep. 17, 2015

(65) Prior Publication Data
US 2016/0084925 A1  Mar. 24, 2016

(30) Foreign Application Priority Data
Sep. 19, 2014  (FR) ...................................... 14 58888

(51) Int. Cl.
*G01R 33/24* (2006.01)
*A61B 5/04* (2006.01)

(52) U.S. Cl.
CPC .......... *G01R 33/24* (2013.01); *A61B 5/04007* (2013.01); *A61B 5/04008* (2013.01)

(58) Field of Classification Search
CPC ........................ A61B 5/04007; A61B 5/04008; G01R 33/24; G01R 33/04; G02F 2001/133638
See application file for complete search history.

(56) References Cited

U.S. PATENT DOCUMENTS 2,975,360 A    3/1961 Bell
5,882,304 A *  3/1999 Ehnholm ............... G01R 33/60
                                                    324/316

(Continued)

FOREIGN PATENT DOCUMENTS

CA      760 579        6/1967
EP      0 463 919 A1   1/1992

(Continued)

OTHER PUBLICATIONS

French Preliminary Search Report dated Jun. 2, 2015 in French Application 14 58888, filed on Sep. 19, 2014 ( with English Translation of Categories of Cited Documents).

(Continued)

*Primary Examiner* — Jay Patidar
(74) *Attorney, Agent, or Firm* — Oblon, McClelland, Maier & Neustadt, L.L.P.

(57) ABSTRACT

A magnetometer including a detector configured to measure the amplitude of an output signal at an oscillation frequency to deduce a component of a magnetic field to be measured starting from the value of a resonance gradient, including a main excitation source outputting a measurement signal oscillating at a main oscillation frequency and a secondary excitation source outputting a reference signal with known amplitude oscillating at a secondary oscillation frequency, the detector being configured to measure the output signal amplitude at a harmonic of the secondary oscillation frequency and to deduce said resonance gradient. The invention also applies to a network of magnetometers and a method of measuring a magnetic field without slaving and compensation of fluctuations of the resonance gradient.

13 Claims, 3 Drawing Sheets

(56) References Cited

U.S. PATENT DOCUMENTS

| | | |
|---|---|---|
| 8,154,349 B2 | 4/2012 | Le Prado et al. |
| 8,183,942 B2 | 5/2012 | Le Prado et al. |
| 8,525,516 B2 | 9/2013 | Le Prado et al. |
| 8,773,120 B2 | 7/2014 | Jager et al. |
| 8,917,091 B2 | 12/2014 | Le Prado et al. |
| 9,025,095 B2 | 5/2015 | Rossini et al. |
| 2013/0027041 A1* | 1/2013 | Savukov ............... G01R 33/26 324/322 |
| 2014/0097837 A1 | 4/2014 | Takahashi |
| 2014/0121491 A1 | 5/2014 | Zhang |
| 2014/0368193 A1 | 12/2014 | Morales et al. |
| 2015/0008916 A1 | 1/2015 | Le Prado et al. |
| 2016/0116553 A1* | 4/2016 | Kim ..................... G01R 33/26 324/305 |

FOREIGN PATENT DOCUMENTS

| | | |
|---|---|---|
| EP | 2 426 563 A1 | 3/2012 |
| FR | 1 591 129 | 4/1970 |

OTHER PUBLICATIONS

J. Dupont-Roc "Etude Theorique De Diverses Resonances Observables En Champ Nul Sur Des Atomes << Habilles>> Par Des Photons de Radiofrequence", Le Journal de Physique, vol. 32, 1971, 10 pages.

J.C. Alldred et al. "Square cross section coils for the production of uniform magnetic fields", J. Sci. Instrum, vol. 44, 1967, 6 pages.

\* cited by examiner

MAGNETOMETER WITHOUT SLAVING AND WITH COMPENSATION FOR FLUCTUATIONS IN THE RESONANCE GRADIENT IN WEAK FIELD, MAGNETOMETERS NETWORK AND MEASUREMENT METHOD

TECHNICAL FIELD

The field of the invention is magnetometers for which the measurement of a magnetic field includes measurement of the amplitude of a signal with a harmonic of an oscillation frequency of an excitation source. The invention applies particularly to saturated core type or vector atomic type magnetometer networks like those used in magnetocardiography or magnetoencephalography.

STATE OF PRIOR ART

Magnetometers are known for which the measurement principle is based on the use of at least one among several harmonics generated by means of an excitation source.

For example this is case for saturated core type magnetometers (also known as "fluxgate" magnetometers) in which an alternating excitation current is applied to an excitation coil surrounding a magnetic core. The magnetic field to be measured induces current pulses in a detection coil that also surrounds the magnetic core, said pulses being resonant at harmonics of the excitation current frequency. The amplitude of even harmonics is proportional to the field to be measured.

This is also the case for vector atomic magnetometers. These magnetometers use a cell full of a gas of atoms, a laser source that emits a beam polarised in the direction of the cell along a propagation direction, and a photodetector capable of outputting an output signal representative of the beam that passed through the cell. A coil surrounds the cell and is powered by a frequency generator to generate a sinusoidally excited magnetic field perpendicular to said propagation direction and parallel to the field to be measured.

A presentation of the operating principle of such atomic magnetometers is given in the article by J. Dupont-Roc, entitled "Etude théorique de diverses résonances observables en champ nul sur des atomes "habillés" par des photons de radiofréquence" (Theoretical study of miscellaneous resonances observable in zero field on atoms "coated" by radiofrequency photons), Le journal de physique, Volume 32, February 1971, p 135.

The signal S captured by the photodetector includes several harmonics given by the following expressions.

$$S = J_0 M + \Sigma_{q \geq 1}(2J_{2q} \cos 2q\omega t) \cdot M - \Sigma_{q \geq 0}(2J_{2q+1} \cos(2q+1)\omega t) \cdot N,$$

in which $$M = \frac{\lambda J_0}{\Gamma} \frac{\Gamma^2 + \omega_x^2}{\Gamma^2 + \omega_x^2 + \omega_y^2 + \omega_z^2},$$

$$N = \frac{\lambda J_0}{\Gamma} \frac{\Gamma \omega_z + \omega_x \omega_y}{\Gamma^2 + \omega_x^2 + \omega_y^2 + \omega_z^2},$$

$\omega_i$ is the magnetic field on axis i multiplied by $\gamma$, the gyromagnetic ratio of the energy level considered for the atom, $\lambda$ describes the orientation induced by optical pumping, $1/\Gamma$ is the relaxation time of the energy level considered for the atom, $J_n$ is the order n Bessel function with argument $$\frac{\gamma B_1}{\omega}.$$

S more particularly contains odd resonances at frequencies $$\frac{(2q+1)\omega}{2\pi}$$

(where q is a positive or zero integer) that are proportional to the magnetic field to be measured on the z axis.

Only the resonance at the frequency of the excitation field $\omega/2\pi$ is actually processed, since the other harmonics are not used. This resonance is present in the weak magnetic field $\omega_i < \Gamma$, where $i \in \{x, y, z\}$. It is used to measure a weak magnetic field by slaving a compensation magnetic field $B_C$ for which the amplitude is adjusted so that the sum $B_C + B_0$ is continuously kept equal to zero. In this way, knowledge of the current Ic injected into the coil to apply the compensation field is sufficient to determine the ambient magnetic field $B_0$ because $Bc = -B_0$.

Magnetometers slaved in a zero magnetic field thus make use of resonant signals observable in a very weak magnetic field. As described above, the operating principle is to generate a compensation magnetic field $B_C$, that will oppose the ambient magnetic field $B_0$. In the context of a network of magnetometers, the compensation magnetic field $B_C$ generated by the coils of a magnetometer also affects the other magnetometers in the network, particularly the closest. It disturbs measurements made by other magnetometers in the network and can lead to instabilities of magnetometers.

In practice, fluxgate or vector atomic type magnetometers are separated by several centimeters when they are installed in a network so that there is no disturbance between them. But such a separation is impossible for applications such as magnetocardiography or magnetoencephalography, in which the network pitch may be as small as 1 to 2 centimeters.

PRESENTATION OF THE INVENTION

The purpose of this invention is to propose a solution other than separation of network sensors to limit interference in a magnetometers network. To achieve this, it proposes a device for measurement of a magnetic field component comprising a detector configured to measure the amplitude of an output signal at an oscillation frequency of an excitation source and to use it to deduce the component of the magnetic field to be measured starting from the value of a resonance gradient characteristic of a proportionality relation between said amplitude and the magnetic field to be measured, characterised in that it comprises a main excitation source outputting a measurement signal oscillating at a main oscillation frequency and a secondary excitation source outputting a reference signal with a known amplitude oscillating at a secondary oscillation frequency different from the main oscillation frequency, and in that the detector is also configured to measure the amplitude of the output signal at a harmonic of the secondary oscillation frequency and to use it to deduce the value of said resonance gradient starting from said amplitude of the output signal at a harmonic of the secondary oscillation frequency and the known amplitude of the reference signal.

The following describes some preferred but non-limitative aspects of this device:

the detector is configured to determine a magnetic reference field generated by the secondary excitation source making use of a transfer function of the secondary excitation source relating the amplitude to the magnetic field;

the secondary excitation source comprises at least one coil and a frequency generator capable of injecting a current with known amplitude into the coil;

the secondary excitation source comprises a plurality of coils each associated with an axis of the device;

the secondary excitation source is configured to output a reference signal onto each of said axes, one by one;

the secondary excitation source is configured to output a reference signal simultaneously on each of said axes, the oscillation frequency of the reference signal output to one axis being different from the oscillation frequency of the reference signal output to another axis, or being in phase quadrature with the reference signal output to another axis;

it also comprises a tertiary excitation source outputting a constant amplitude compensation signal oscillating at the main oscillation frequency.

The invention also relates to an instrument for measurement of the magnetic field including a plurality of devices according to the first aspect of the invention arranged in a network. In such an instrument, the secondary excitation source of a device may be specific to said device. It may also comprise a secondary excitation source common to said devices. The invention also relates to a method of measuring a component of a magnetic field.

BRIEF DESCRIPTION OF THE DRAWINGS

Other aspects, purposes, advantages and characteristics of the invention will become clearer after reading the following detailed description of preferred embodiments of the invention given as non-limitative examples with reference to the appended drawings in which.

DETAILED PRESENTATION OF PARTICULAR EMBODIMENTS

Figure 1:
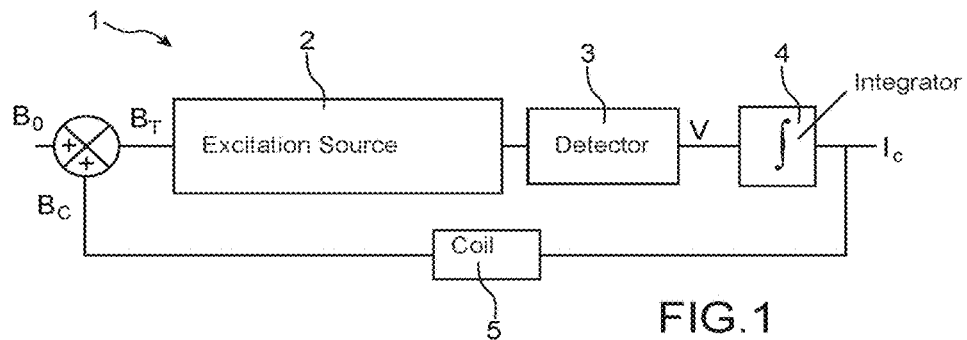
FIG. 1 shows the principle of slaving in a zero magnetic field used with magnetometers according to prior art.

Slaving in zero field shown in FIG. 1 is traditionally used to make the measurement of the magnetic field $B_0$. The measurement device 1 comprises an excitation source 2 that enables resonance, for example a coil surrounding the cell and powered by a frequency generator in the case of a vector atomic magnetometer, and a detector 3 for measuring the amplitude of an output signal at a harmonic of the oscillation frequency of the excitation source.

This amplitude and the current value calculated from this amplitude by means of an integrator 4 cancel out for a total magnetic field $B_T$ equal to zero. This is done by applying the compensation magnetic field $B_C$ through a coil 5 powered by a current $I_C$. The current $I_C$ injected into the coil 5 is measured and the current/magnetic field transfer function of the coil is used to determine the value of the compensation magnetic field $B_C$ and therefore of the ambient field $B_0$.

Slaving described with reference to FIG. 1 is necessary for each magnetometer measurement axis. Thus, three slavings of this type are necessary in order to measure the three components of the ambient field $B_0$.

Figure 2:
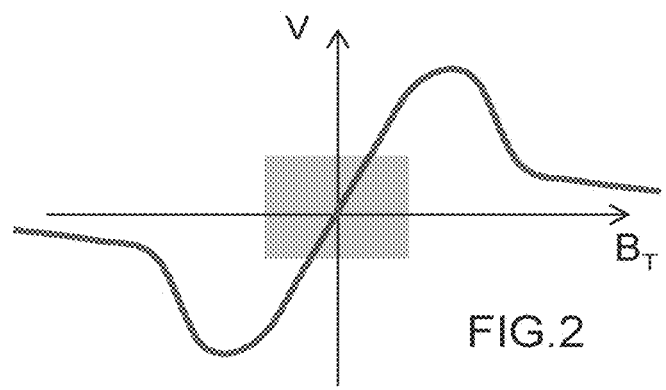
FIG. 2 shows the linear portion of the resonance curve observable in the presence of a weak magnetic field.

FIG. 2 shows the resonance curve representing the amplitude V of the signal measured by the detector 3 as a function of the total magnetic field $B_T$. This curve has a linear portion when the magnetic field is weak and close to which the amplitude is directly proportional to the magnetic field.

Considering that the amplitude of magnetic signals from the heart or the brain is less than 1 nT, namely very much lower than the range of the linear portion of the resonance curve that is a few tens of nT for a vector atomic magnetometer and a few hundreds of µT for a fluxgate type magnetometer, the invention proposes to not use slaving in zero magnetic field but to measure the ambient magnetic field $B_0$ directly through the measurement of the amplitude V of the resonance and through knowledge of the gradient of the linear portion of the resonance curve.

Figure 3:
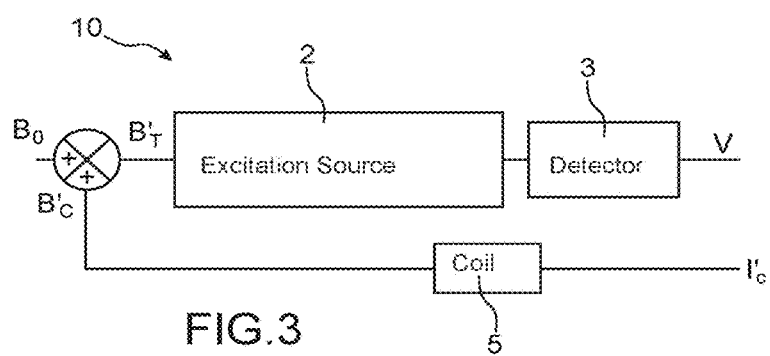
FIG. 3 shows the principle of measurement without slaving in a zero magnetic field used with magnetometers according to the invention.

FIG. 3 shows the principle of measurement without slaving in zero field used by magnetometers according to the invention. The measurement device 10 according to the invention contains the excitation source 2 and the detector 3 described above.

In one possible embodiment shown in FIG. 3, the ambient field $B_0$ may be compensated in advance, particularly if it is too strong to guarantee use of resonances on their linear portion. A constant current $I'_C$ is injected into the coil 5 for this purpose to generate a constant compensation field $B'_C$ such that the measured field $B'_T=B_0+B'_C$ is sufficiently weak to guarantee resonance in the linear portion.

It will be understood that for the purposes of the invention, the magnetic field to be measured is a field for which the amplitude guarantees resonance in the linear portion. It may be the ambient field $B_0$ (for example for magnetic signals output from the heart or the brain) or the compensated ambient field $B'_T$ as mentioned above to guarantee resonance in the linear portion.

Thus, the invention relates to a device 10 for measuring a component of a magnetic field comprising a detector 3 configured to measure the amplitude V of an output signal at an oscillation frequency of an excitation source 2 and to use it to deduce the magnetic field $B'_T$ to be measured from said amplitude and the value of a resonance gradient characteristic of a proportionality relation between said amplitude and the component of the magnetic field to be measured (field $B_0$ or $B'_T$ depending on whether or not compensation is necessary to obtain this proportionality relation).

Interference between magnetometers in a magnetometers network is eliminated in the absence of zero field slaving. However, the resonance gradient that is used to determine the magnetic field starting from the measurement of the amplitude of the resonance depends on several parameters that vary with time. For example, this includes the laser power, the temperature, and displacements of optical fibres for the vector atomic magnetometer. Resonance gradients specific to each magnetometer in a network can vary significantly and independently of each other and can cause errors in magnetic source reconstruction algorithms used for example in magnetocardiography or magnetoencephalography.

The invention discloses a technique to control the impact of the variation of the resonance gradient, so as to calibrate the magnetometers. With this technique, a reference signal having an amplitude which is known and sufficiently weak relative to the extent of the linear portion of the resonance curve is imposed on a magnetometer. The amplitude of the resonance induced by this reference signal can be used to return the value of the resonance gradient.

The invention thus proposes a device for measurement of a magnetic field like that described above and characterised in that it comprises a main excitation source outputting a measurement signal oscillating at a main oscillation frequency and a secondary excitation source outputting a reference signal with a known amplitude oscillating at a secondary oscillation frequency different from the main oscillation frequency, the detector also being configured to measure the amplitude of the output signal at a harmonic of the secondary oscillation frequency and to use it to deduce said resonance gradient starting from said amplitude of the output signal at a harmonic of the secondary oscillation frequency and with a known amplitude of the reference signal.

Knowing the resonance gradient, the detector can then deduce the value of the component of the field to be measured starting from the measurement of the amplitude of the output signal at a harmonic of the main oscillation frequency.

The device may also include a tertiary excitation source outputting a compensation signal with a constant amplitude oscillating at the main oscillation frequency. This source can generate a constant compensation field $B'_C$.

Figure 4:
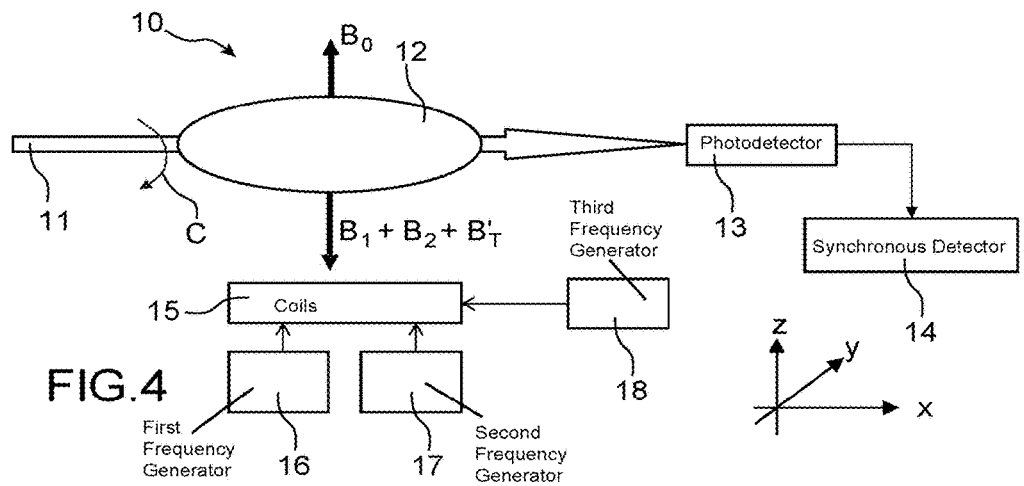
FIG. 4 is a diagram of an atomic magnetometer with parametric resonance in a zero field according to one possible embodiment of the invention.

FIG. 4 shows a diagram of an atomic magnetometer with parametric resonance in zero field according to one possible embodiment of the invention. The magnetometer comprises a laser emitting a beam 11, a circular polariser C outputting a circularly polarised beam, a cell 12 filled for example with helium-4, a photodetector 13 receiving the beam that passed through the cell 12, a synchronous detector 14 adjusted firstly to a harmonic of the main oscillation frequency and secondly to a harmonic of the secondary oscillation frequency.

The magnetometer also comprises coils 15 powered by frequency generators 16, 17, 18. A first frequency generator 16 can be used to generate the main excitation magnetic field B1 (measurement field), a second frequency generator 17 can be used to generate the secondary excitation magnetic field B2 with known amplitude (reference field) and in one possible variant embodiment, a third frequency generator 18 can be used to generate a constant compensation magnetic field $B'_C$ as described above.

In the context of the invention, the detector is more precisely configured to determine the reference magnetic field B2 generated by the secondary excitation source making use of an excitation source transfer function relating the amplitude to the magnetic field.

The secondary excitation source may for example include at least one coil 15, usually a plurality of coils each associated with one axis of the magnetometer, and a frequency generator 17 that injects a current with a known amplitude into the coil. The current/magnetic field transfer function of a coil used in a fluxgate or vector atomic magnetometer can be determined precisely, for example using the method disclosed in document EP2426563A1 for an atomic magnetometer.

In a first embodiment of the invention as shown in FIG. 4, the secondary excitation source uses coils that are already installed on each magnetometer. The reference signal with known amplitude is used to apply a magnetic field in a frequency band discontiguous from signals of interest for the application (from 0 to 0.1 Hz, or beyond 100 Hz for magnetocardiography or magnetoencephalography) and is used to determine the value of the resonance gradient associated with the coil that generates the magnetic field through the measurement of the amplitude of resonance at a harmonic of the secondary oscillation frequency, in real time.

This approach is possible for all axes of a magnetometer (to determine all the components of the magnetic field to be measured) and for all magnetometers in a network when applicable.

In a first variant, the secondary excitation source is configured to output the same reference signal individually on each of said axes one by one.

Figure 5:
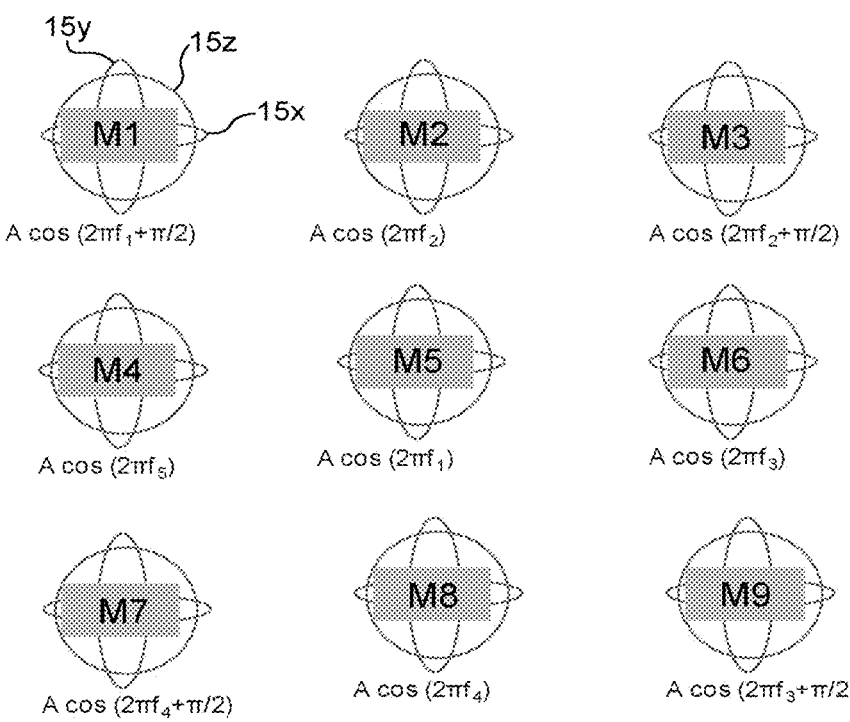
FIG. 5 shows reference signals used in an open loop magnetometers network according to a first possible embodiment of the invention.

In a second variant, particularly in which a real time calibration is made possible, the secondary excitation source is configured to output a reference signal on each of said axes simultaneously, the oscillation frequency of the reference signal output to one axis being different from the oscillation frequency of the reference signal output to another axis, or being in phase quadrature with the reference signal output to another axis. It is necessary that the reference signals seen by a magnetometer are not superposed on reference signals generated by adjacent magnetometers. The reference signals then have to be "orthogonal", either at different frequencies or in phase quadrature, for example to reduce the number of frequencies used. In this respect, FIG. 5 shows examples of reference signals used in a network of nine magnetometers M1-M9 in open loop according to this second variant of the first possible embodiment of the invention. Reference signal in phase quadrature are used in this case to limit the number of frequencies f1-f5 used to five. For each of the magnetometers, the coils 15x, 15y, 15z are used to apply a reference signal to each of the three axes.

Note that this network of nine magnetometers can be repeated. This assures that the closest neighbours do not disturb each other. This technique can also take account of the case of second rank neighbours. New frequencies, or in any case other reference signals orthogonal to the reference signals in the first series, may be used for this purpose. It will be noted that this technique can also be used in a network of magnetometers developed in three dimensions rather than in two dimensions as in the example in FIG. 5.

Thus, the invention is also applicable to a magnetic field measurement instrument comprising a plurality of measurement devices like those described above that are arranged in a network, an instrument in which the secondary excitation source of a device is specific to said device. The secondary excitation sources of said devices may in particular be configured to output said reference signal to each device one by one. And the secondary excitation source and the main excitation source of a device preferably comprise at least one coil in common.

Figure 6:
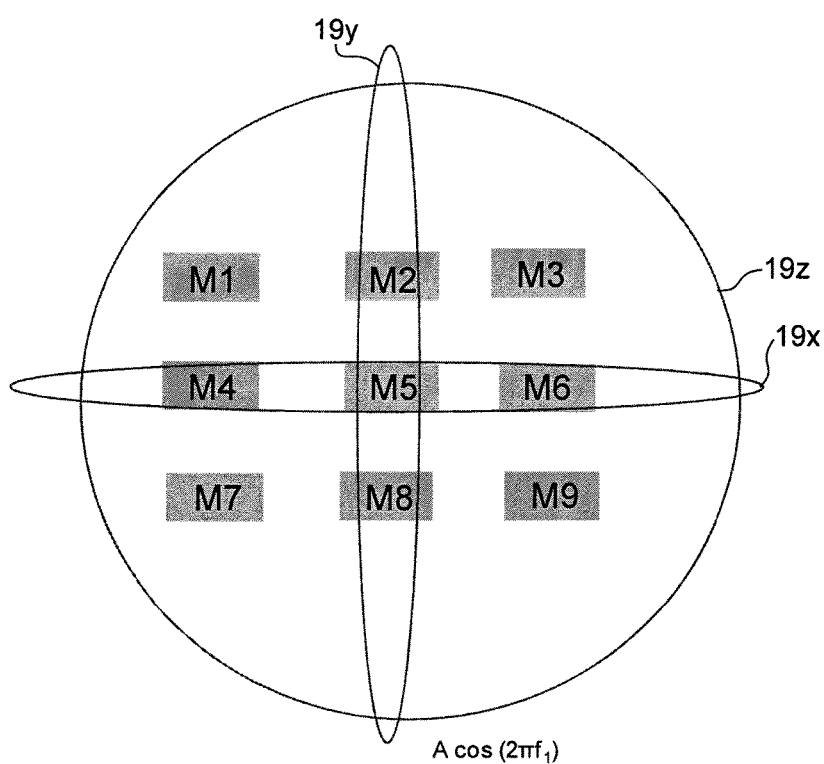
FIG. 6 shows reference signals used in an open loop magnetometers network according to a second possible embodiment of the invention.

In a second embodiment of the invention like this shown in FIG. 6, the secondary excitation circuit is configured to generate a reference signal common to all magnetometers by means of coils designed to produce a "common" magnetic field at the scale of the network. The invention is thus applicable to a magnetic field measurement instrument comprising a plurality of devices M1-M9 as described above arranged in a network, instrument in which the secondary excitation source is common to said devices. The secondary excitation source may in particular include at least one coil 19x, 19y, 19z surrounding the instrument M1-M9 and a frequency generator used to inject a current with known amplitude into the coil. A different frequency can be adopted for each axis.

This second embodiment has the advantage that it enables calibration of alignment defects of network magnetometers. However, it suffers from the need to add an additional assembly to the network, therefore making it larger and more expensive.

The following description relates to an example embodiment of the invention in which the magnetometers in the network are vector atomic magnetometers. The gradients of their resonances are 10 mV/nT on the X and Y axes and 3 mV/nT for the Z axis. The linear part of resonances is limited to ±5 nT. Sensitive elements of the magnetometers are rectangular parallelepipeds with side dimensions of 2 cm. The pitch of the surface network of magnetometers is equal to 5 mm. It is composed of nine magnetometers distributed as shown in FIGS. 5 and 6. The magnetic field at the location of the network is [0, 0, 10] nT on the [X, Y, Z] axes.

In the context of implementation of the first embodiment of the invention, the geometry of the coils can be used to generate homogeneous magnetic fields. In this case, the parameters of this geometry described in the article by J. C. Alldred et al. entitled "Square cross section coils for the production of uniform magnetic fields", J. Sci. Instrum., 1967, Vol. 44, are $a_1=0.955$, $a_2=1.000$, $h_1=1.051$, $h_2=0.288$, $N_1=21/11$, $N_2=1$.

The magnetic field generated is equal to $B=100 \times 1.83 \ 10^{-4}$ T/A, with a homogeneity of less than $10^{-3}$ in a 1 cm radius sphere. The homogeneity of the generated field has a direct impact on the uncertainty of the transfer function in open loop that will be set up at the end of the process and for which targeted knowledge is within $10^{-2}$. The architecture of the chosen coils is therefore comfortable with respect to this objective.

Therefore, the coil transfer functions are 18.3 nT/μA, for each of the 3 axes of the magnetometers. The magnetometer at the centre of the network is firstly slaved in zero field. It measures the magnetic field of [0, 0, 10] nT and compensates it with currents of [0, 0, 0.54] μA injected into its coils. The applied currents are maintained but slaving is stopped.

The target application is magnetocardiography. The energy of the magnetic signature of heart beats is essentially higher than 0.5 Hz. Values of 0.40, 0.35, 0.30, 0.25 and 0.20 Hz are chosen for frequencies $f_1$, $f_2$, $f_3$, $f_4$ and $f_5$, defined according to FIG. 5. The values of phases are also as defined in FIG. 5.

The reference signals are chosen to be sinusoidal with the same amplitude corresponding to 1 nT, namely currents of 0.054 μA at the input to the coils.

For implementation of the second embodiment of the invention, the coils used have the same architecture as in the first embodiment but with 2 m sides so as to contain the magnetometers network and the patient. Their transfer function is equal to $1.83 \ 10^{-4}$ T/A. The chosen reference signals are sinusoidal signals at the same frequency, for example $f_1=0.2$ Hz, and with the same amplitude corresponding to 1 nT, giving currents of 5.4 μA at the input to the coils.

In each of these embodiments, a synchronous detection is made for each magnetometer axis to quantify the impact of the reference signal in open loop. The voltage measured at the synchronous detections changes in real time (resonance gradients are not constant in time), within the [10±1, 10±1, 3±0.5] mV range on the X, Y, Z axes respectively for references with an amplitude of 1 nT. It can thus be used to determine the variation of gradients of magnetometer axes equal to [10±1, 10±1, 3±0.5] mV/nT during the measurement and thus the transfer function of the magnetometer operated in open loop.

The invention is not limited to a magnetometer or a network of magnetometers as described above but also includes a method of measuring a component of a magnetic field using such a magnetometer or network of magnetometers, and particularly a method making use of a measurement of the amplitude of an output signal at an oscillation frequency of an excitation source and determination of the component of the magnetic field to be measured making use of the value of a resonance gradient characteristic of a proportionality relation between said amplitude and the magnetic field component to be measured, the method being characterised by superposition on a measurement oscillating signal at the main oscillation frequency, of a reference signal with known amplitude oscillating at a secondary oscillation frequency different from the main oscillation frequency, by measuring the amplitude of the output signal at a harmonic of the secondary oscillation frequency and by determination of said resonance gradient starting from said amplitude of the output signal at a harmonic of the secondary oscillation frequency and at a known amplitude of the reference signal.

The invention claimed is:

1. A device for measurement of a magnetic field component comprising a synchronous detector configured to measure an amplitude of a photodetector signal at an oscillation frequency of an excitation source and to deduce the component of the magnetic field to be measured starting from a value of a resonance gradient characteristic of a proportionality relation between said amplitude and the component of magnetic field to be measured, wherein the device further comprises a main excitation source outputting a measurement signal oscillating at a main oscillation frequency and a secondary excitation source outputting a reference signal with a known amplitude oscillating at a secondary oscillation frequency different from the main oscillation frequency, and wherein the synchronous detector is also configured to measure the amplitude of the photodetector signal at a harmonic of the secondary oscillation frequency and to use it to deduce the value of said resonance gradient starting from said amplitude of the photodetector signal at a harmonic of the secondary oscillation frequency and the known amplitude of the reference signal.

2. The device according to claim 1, in which the synchronous detector is configured to determine a magnetic reference field generated by the secondary excitation source making use of a transfer function of the secondary excitation source relating the amplitude to the magnetic field.

3. The device according to claim 2, in which the secondary excitation source comprises at least one coil and a frequency generator injecting a current with known amplitude into the coil.

4. The device according to claim 3 having three measurement axes, in which the secondary excitation source comprises coils associated with each of said measurement.

5. The device according to claim 4, in which the secondary excitation source is configured to output a reference magnetic field as the reference signal, said reference magnetic field having three components each corresponding to one of said measurement axes, the three components of the reference magnetic field being outputted one by one.

6. The device according to claim 4, in which the secondary excitation source is configured to output a reference magnetic field as the reference signal, said reference magnetic field having three components each corresponding to one of said measurement axes, the three components of the reference magnetic field being outputted simultaneously, the oscillation frequency of a component of the reference magnetic field being different from the oscillation frequency of another component of the reference magnetic field, or being in phase quadrature with another component of the reference magnetic field.

7. The device according to claim 1, further comprising a tertiary excitation source outputting a constant amplitude compensation signal oscillating at the main oscillation frequency.

8. An instrument for measurement of the magnetic field including a plurality of devices according to claim 1, arranged in a network, in which each device has its own secondary excitation source.

9. The instrument according to claim 8, in which the secondary excitation sources of said devices are configured to output said reference signal to each device one by one.

10. The instrument according to claim 8, in which the secondary excitation source and the main excitation source of a device comprise at least one coil in common.

11. An instrument for measurement of the magnetic field comprising a plurality of devices according to claim 1, arranged in a network, comprising a secondary excitation source common to said devices.

12. The instrument according to claim 11, in which the secondary excitation source includes at least one coil surrounding the network of devices and a frequency generator used to inject a current with known amplitude into the coil.

13. A method of measuring a component of a magnetic field making use of a measurement of an amplitude of a photodetector signal at an oscillation frequency of an excitation source and determination of the component of the magnetic field to be measured making use of a value of a resonance gradient characteristic of a proportionality relation between said amplitude and the component of the magnetic field to be measured, comprising the steps of:

superimposing, on a measurement signal oscillating at a main oscillation frequency, a reference signal with known amplitude oscillating at a secondary oscillation frequency different from the main oscillation frequency, measuring the amplitude of the photodetector signal at a harmonic of the secondary oscillation frequency, and determining said resonance gradient starting from said amplitude of the photodetector signal at a harmonic of the secondary oscillation frequency and at the known amplitude of the reference signal.

* * * * *